United States Patent
Zhang et al.

(10) Patent No.: US 11,813,232 B2
(45) Date of Patent: *Nov. 14, 2023

(54) ANALOGS OF DEUTETRABENAZINE, THEIR PREPARATION AND USE

(71) Applicant: AUSPEX PHARMACEUTICALS, INC., Parsippany, NJ (US)

(72) Inventors: Chengzhi Zhang, San Diego, CA (US); James Kerr, North Wales, PA (US)

(73) Assignee: Auspex Pharmaceuticals, Inc., Parsippany, NJ (US)

(*) Notice: Subject to any disclaimer, the term of this patent is extended or adjusted under 35 U.S.C. 154(b) by 95 days.

This patent is subject to a terminal disclaimer.

(21) Appl. No.: 15/922,329

(22) Filed: Mar. 15, 2018

(65) Prior Publication Data

US 2018/0263972 A1 Sep. 20, 2018

Related U.S. Application Data

(60) Provisional application No. 62/471,484, filed on Mar. 15, 2017.

(51) Int. Cl.
*A61K 31/4745* (2006.01)
*A61P 25/14* (2006.01)
*A61P 25/28* (2006.01)
*C07D 471/04* (2006.01)
*A61K 31/473* (2006.01)

(52) U.S. Cl.
CPC ........ *A61K 31/4745* (2013.01); *A61K 31/473* (2013.01); *A61P 25/14* (2018.01); *A61P 25/28* (2018.01); *C07D 471/04* (2013.01)

(58) Field of Classification Search
None
See application file for complete search history.

(56) References Cited

U.S. PATENT DOCUMENTS

| | | | |
|---|---|---|---|
| 8,524,733 B2 | 9/2013 | Gant et al. | |
| 9,233,959 B2 | 1/2016 | Sommer et al. | |
| 2015/0152099 A1* | 6/2015 | Zhang | C07C 221/00 546/95 |
| 2016/0222008 A1* | 8/2016 | Sommer | A61P 25/18 |
| 2016/0287574 A1 | 10/2016 | Stamler et al. | |
| 2020/0000794 A1 | 1/2020 | Gant et al. | |

FOREIGN PATENT DOCUMENTS

| | | | |
|---|---|---|---|
| CN | 102186848 A | 9/2011 | |
| CN | 103003275 A | 3/2013 | |
| WO | 2010/044981 A3 | 6/2010 | |
| WO | 2011/153157 A3 | 4/2012 | |
| WO | WO-2012081031 A1 * | 6/2012 | ........... C07C 233/18 |

OTHER PUBLICATIONS

FDA Guidance to Industry, "Q7 Good Manufacturing Practice Guidance for Active Pharmaceutical Ingredients," Sep. 2016 (Year: 2016).*
Malik et al. "HPLC: an Analytical Technique for Pharmaceutical Validation of Omeprazole," Journal of Engineering, Computers & Applied Sciences, vol. 2, No. 10, Oct. 2013. (Year: 2013).*
Bourezg et al. "Structural elucidation of two photolytic degradation products of tetrabenazine," Journal of Pharmaceutical and Biomedical Analysis 91 (2014) 138-143 (Year: 2014).*
Savani et al., Neurology 2007, 68(10), 797.
Kenney et al., Expert Review of Neurotherapeutics 2006, 6(1), 7-17.
Jankovic et al. "Deutetrabenazine in Tics Associated with Tourette Syndrome," Tremor Other Hyperkinet. Mov. 2016; 1-8.
Balaji, et al.; "Development and Validation of a new simple and Stability indicating RP-HPLC Method for the determination of Tetrabenazine and its forced degradation impurities in Bulk Drug and Pharmaceutical Dosage form", International Journal of PharmTech Research, vol. 6, No. 3, 2014, pp. 1003-1010.

* cited by examiner

*Primary Examiner* — Jeffrey S Lundgren
*Assistant Examiner* — Michael J Schmitt
(74) *Attorney, Agent, or Firm* — BakerHostetler

(57) ABSTRACT

The disclosure is directed to deutetrabenazine analogs, compositions comprising same and methods of detecting same in compositions comprising deutetrabenazine.

7 Claims, 8 Drawing Sheets

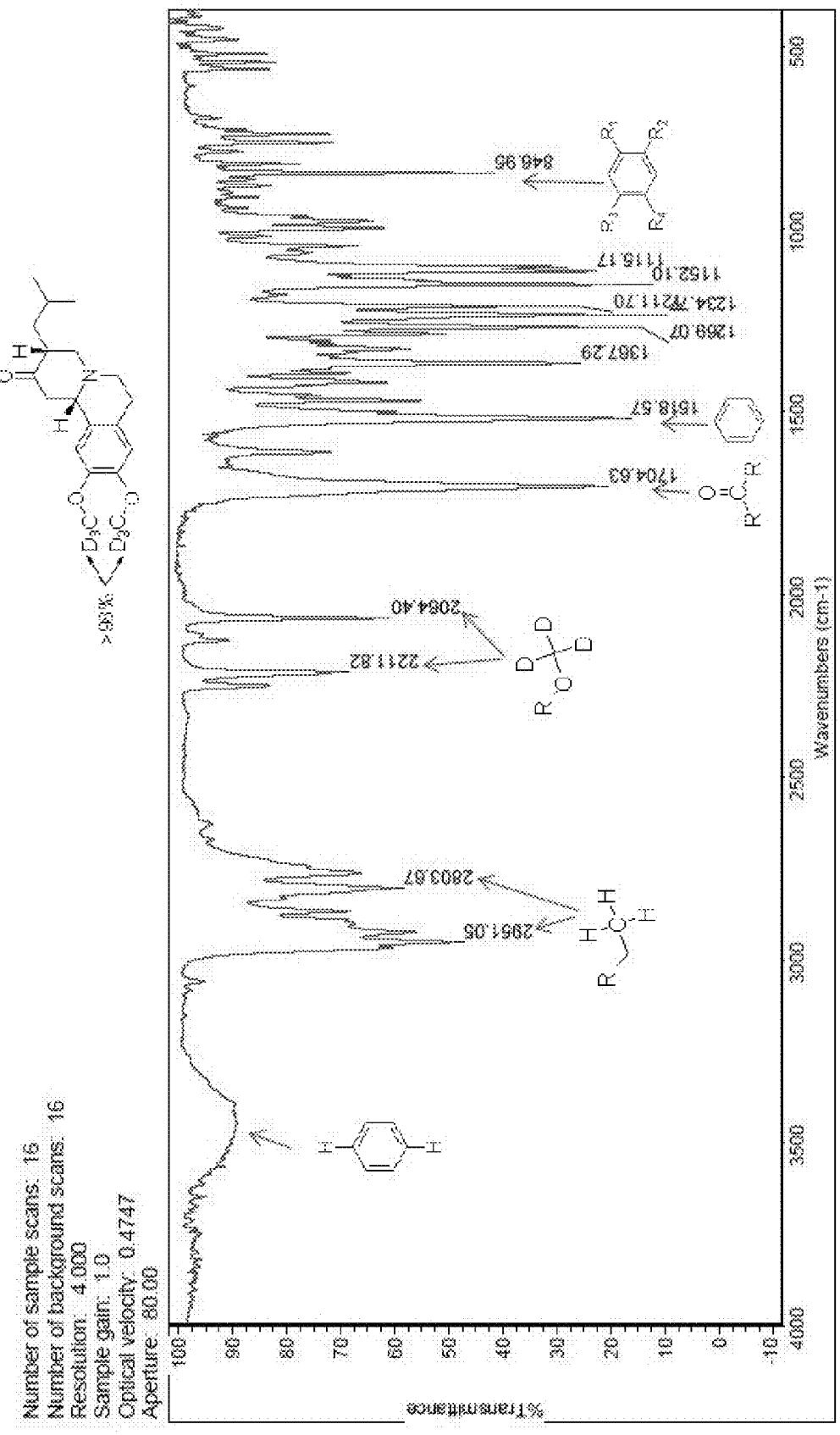
Figure 1: FTIR Spectra of compound 1

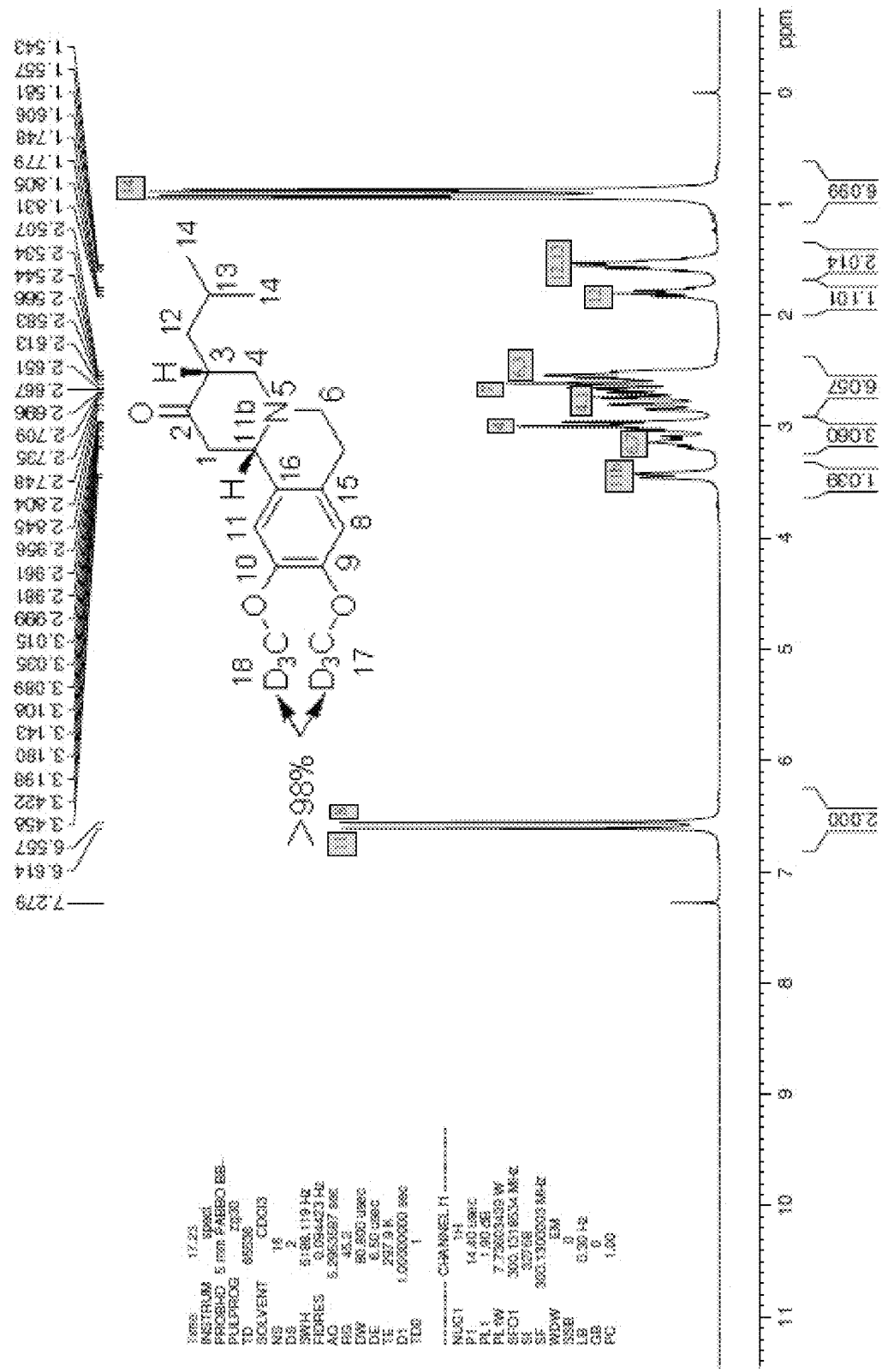
Figure 2: ¹H NMR of compound 1

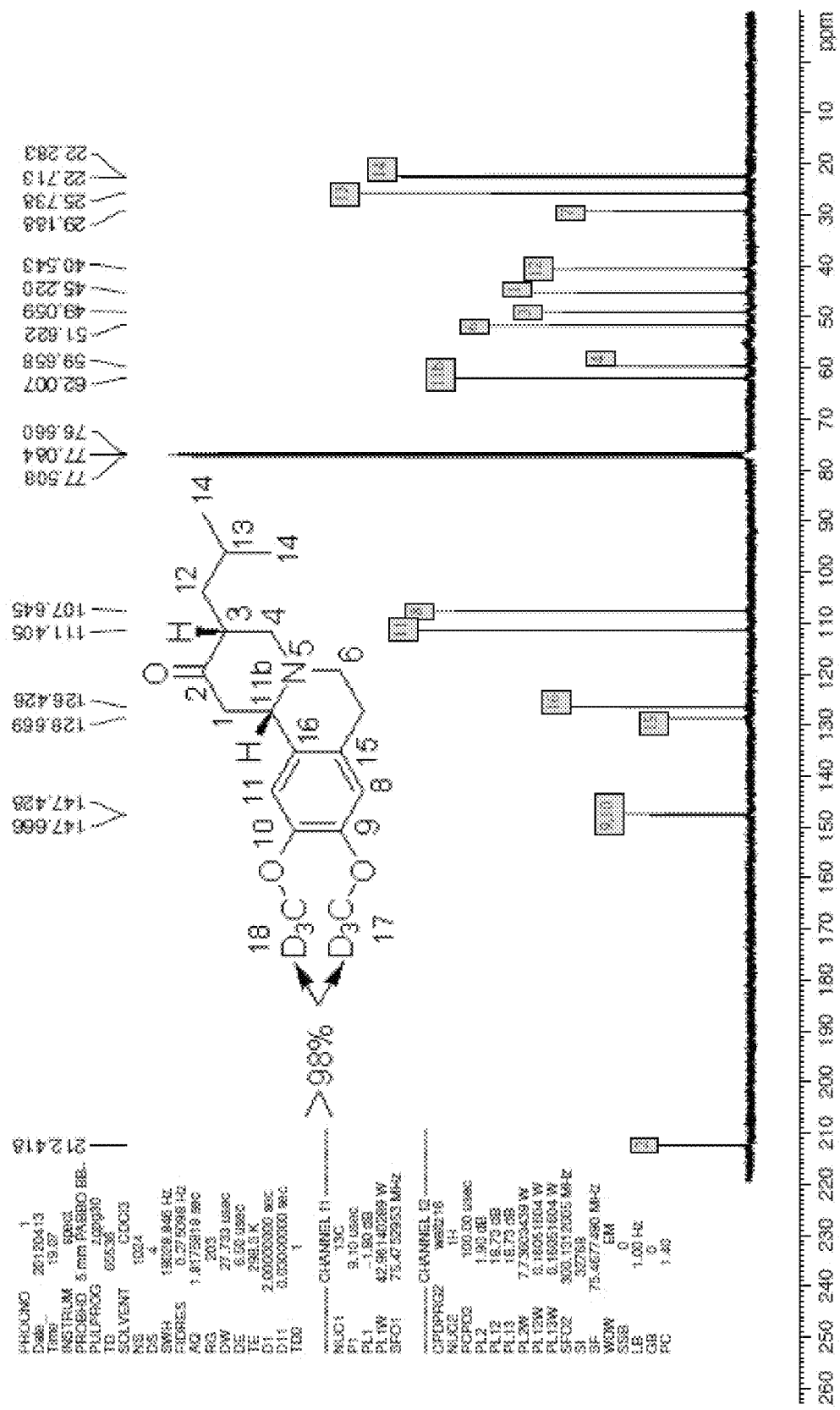
Figure 3: $^{13}$C NMR of compound 1

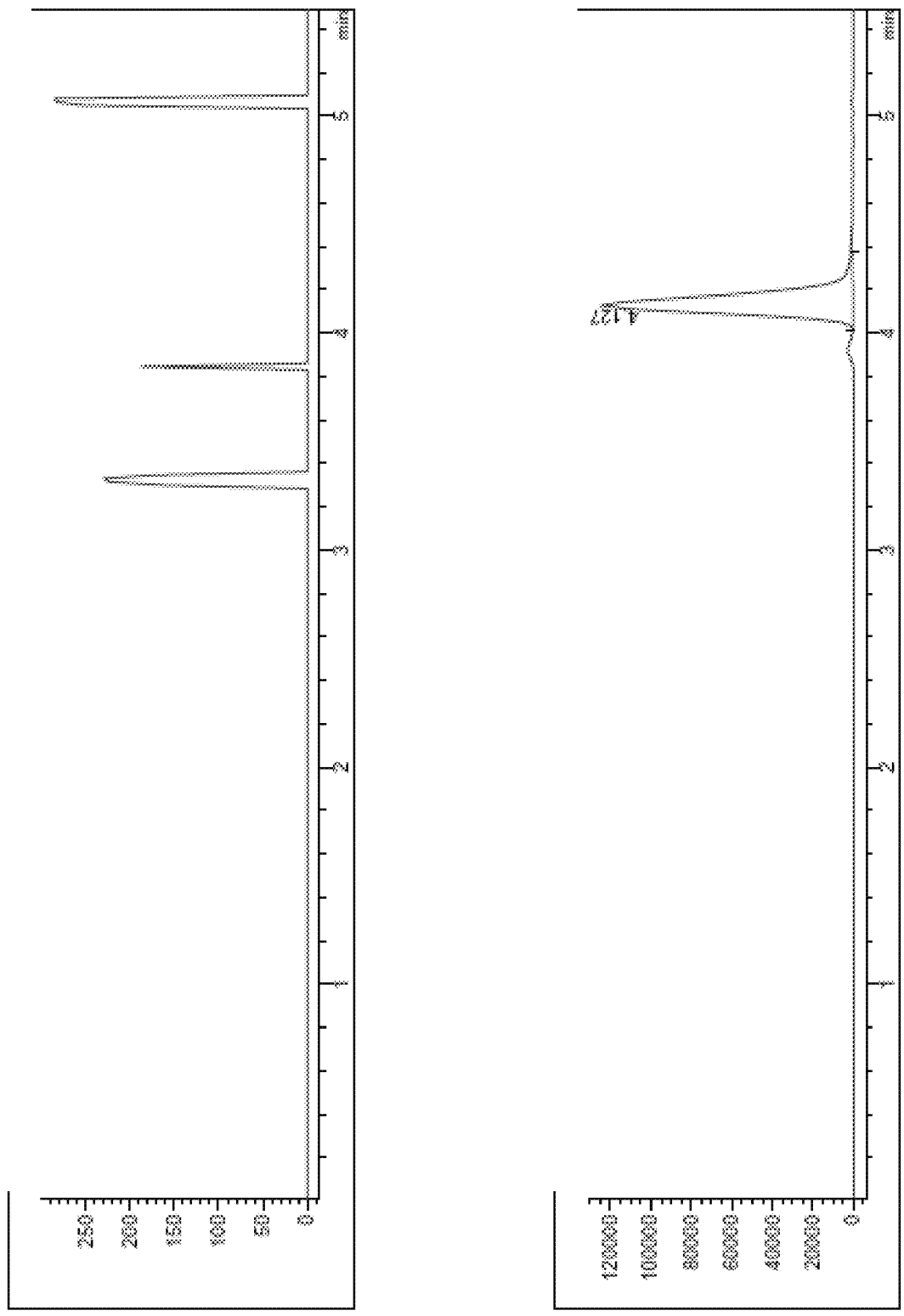
Figure 4: Typical Chromatogram of compound 1.

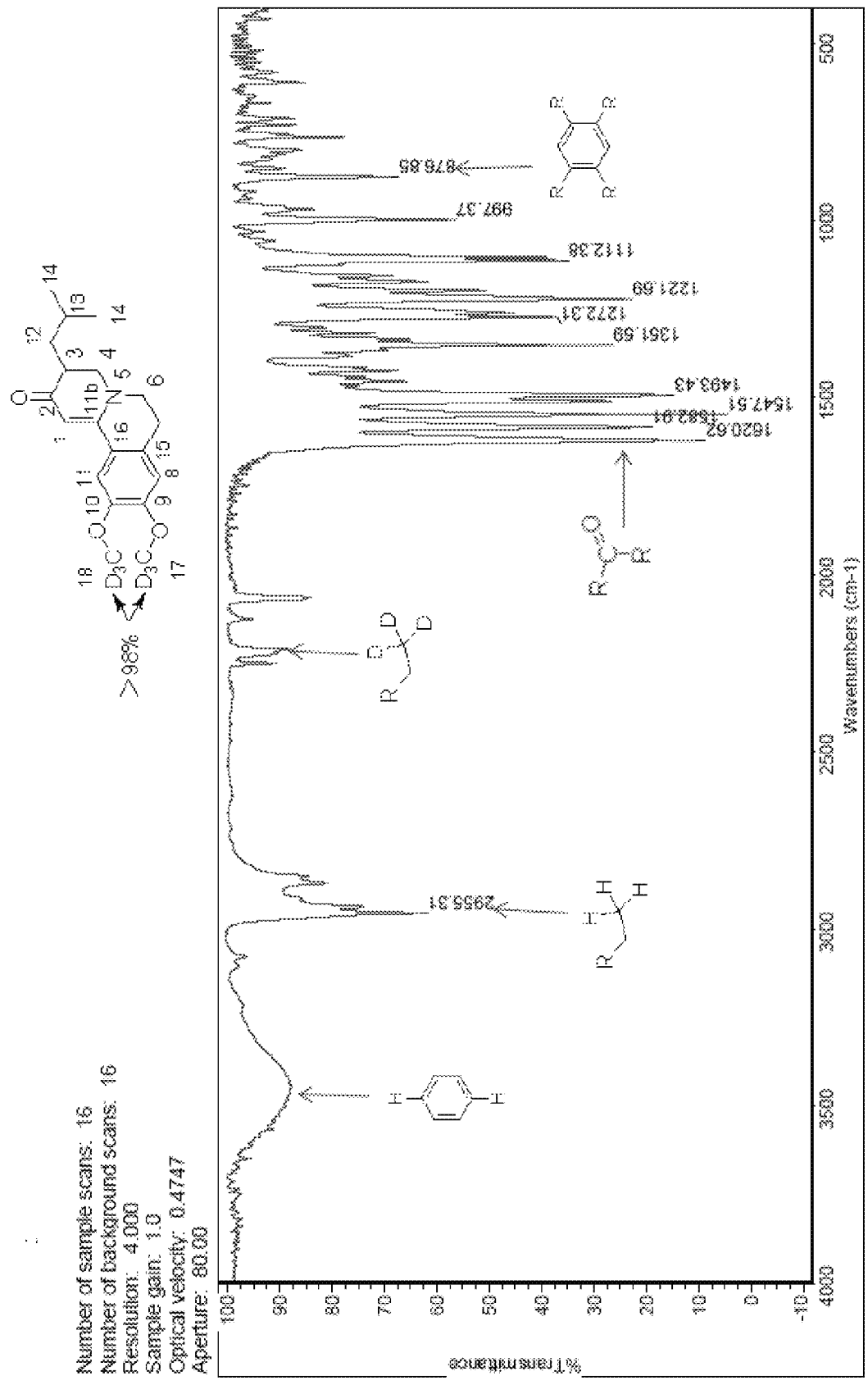
Figure 5: FTIR Spectra of compound 2.

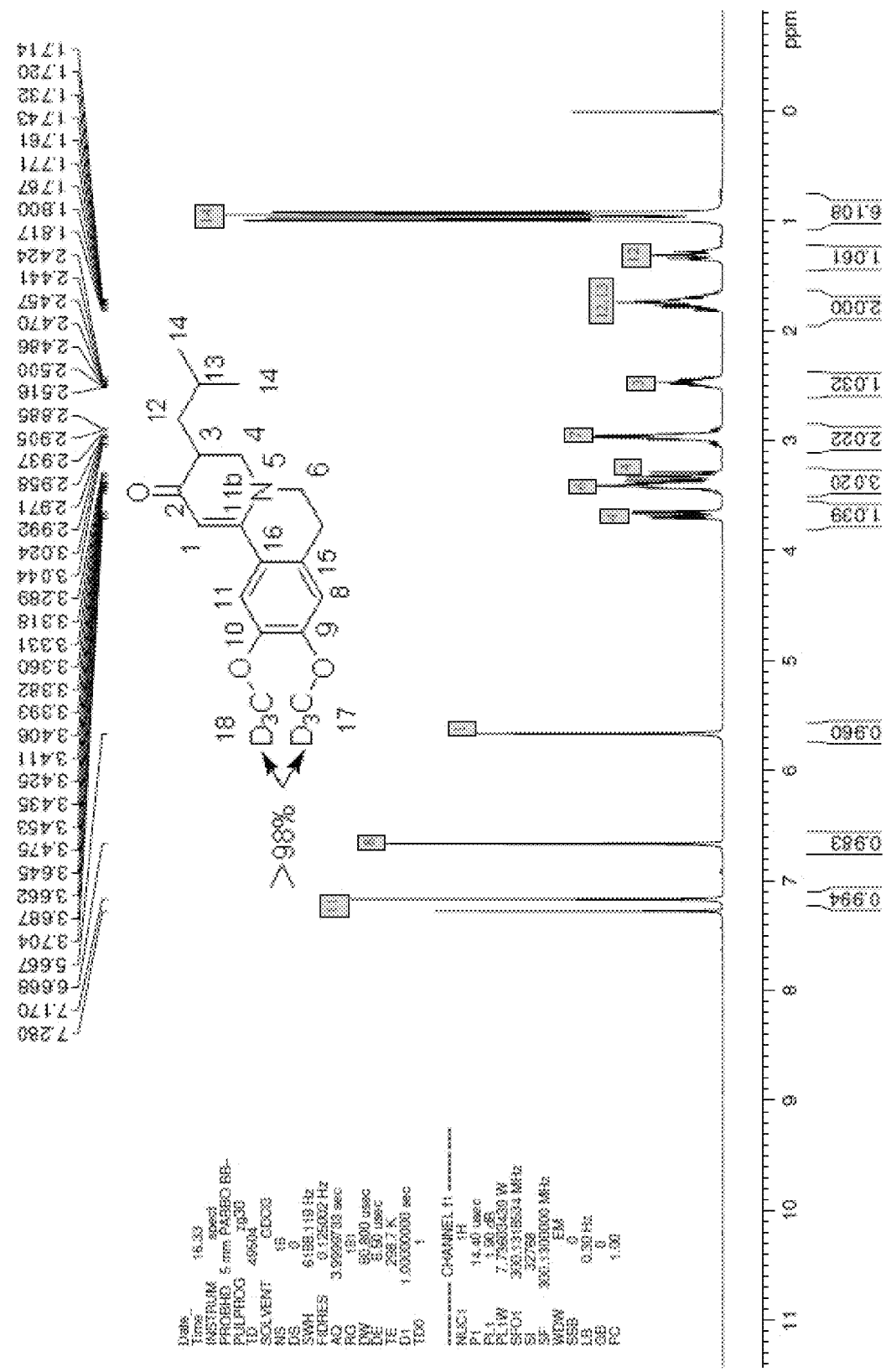
Figure 6: $^1$H NMR of compound 2

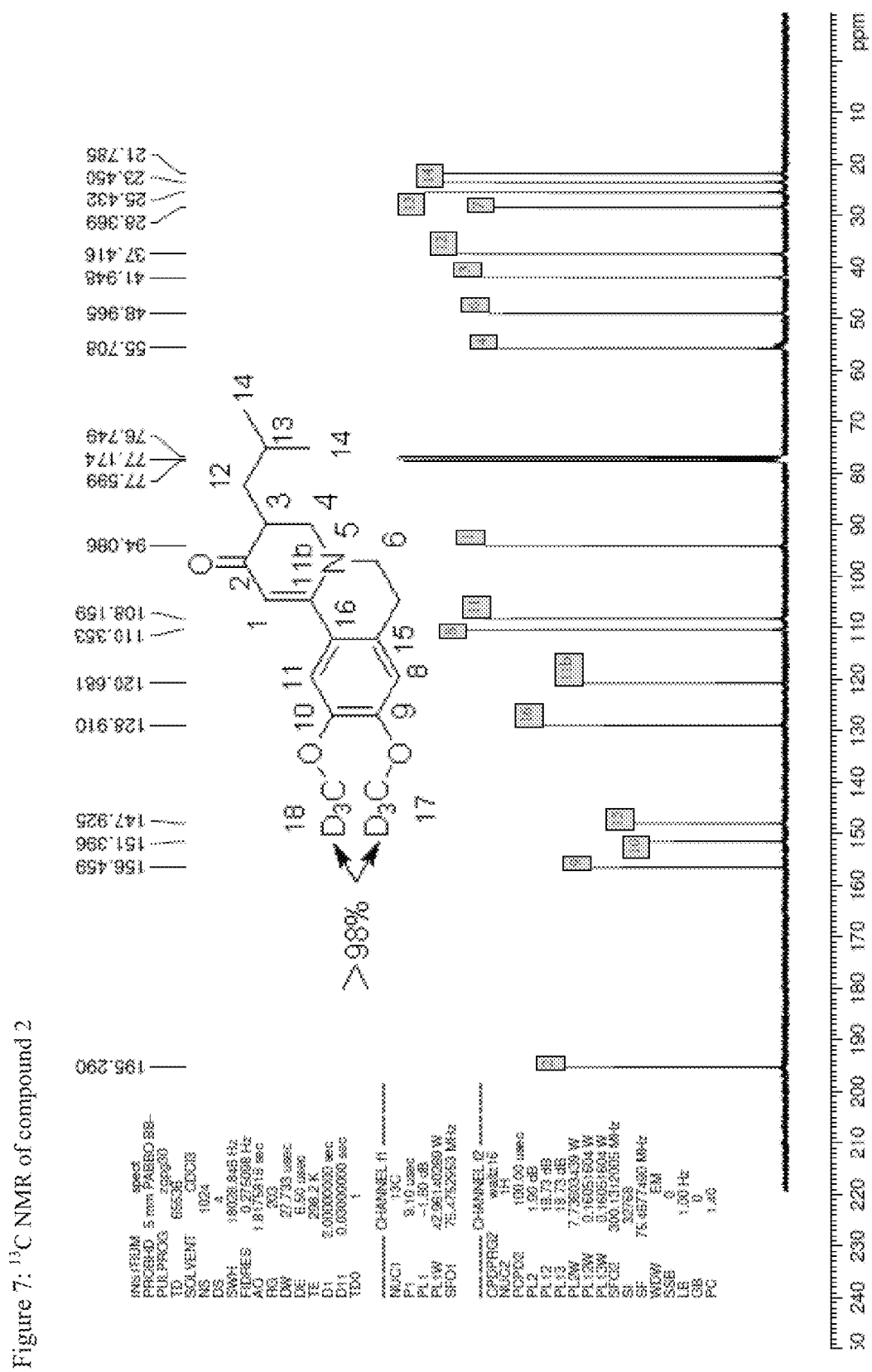
Figure 7: $^{13}$C NMR of compound 2

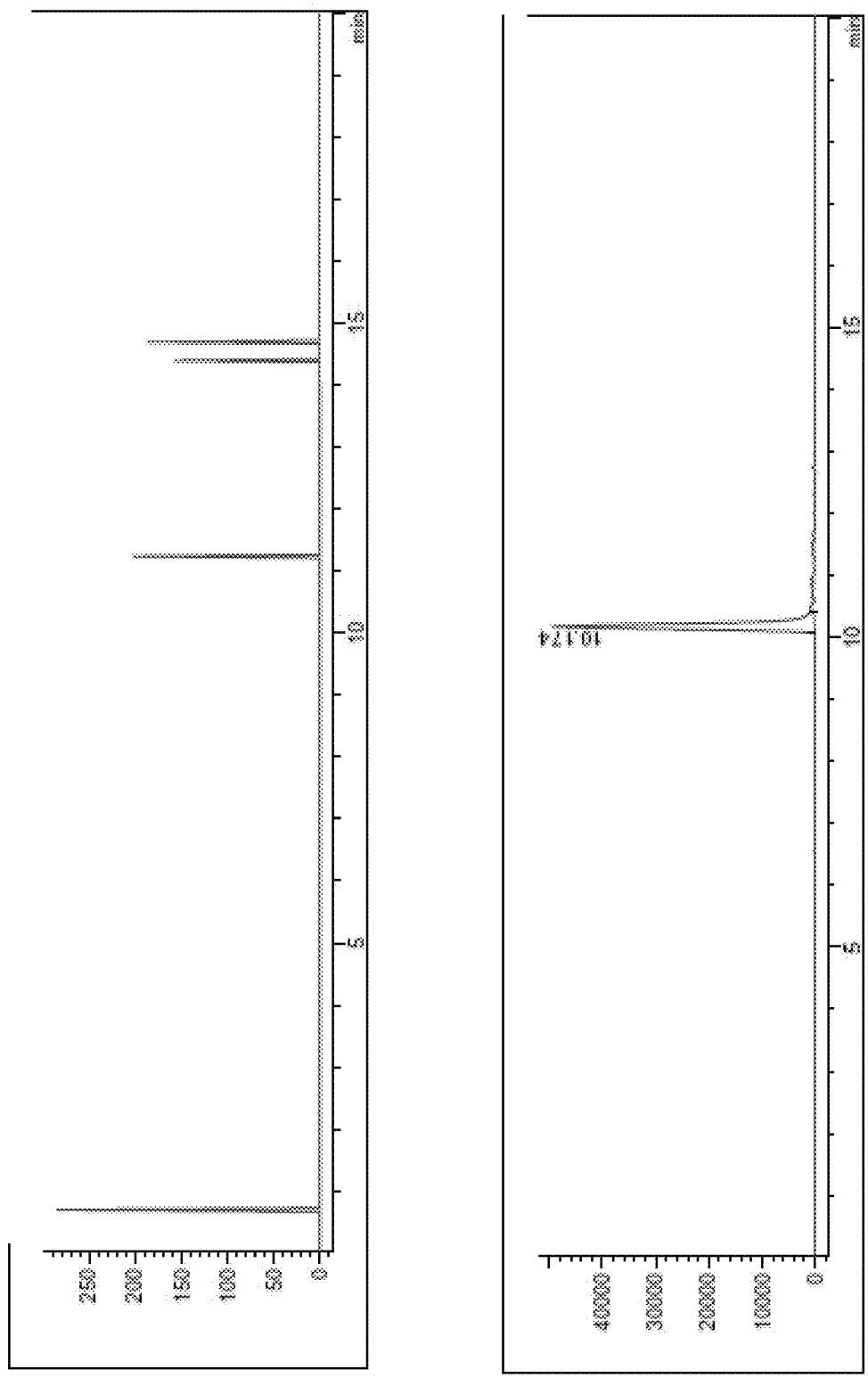
Figure 8: Typical Chromatogram of compound 2.

ANALOGS OF DEUTETRABENAZINE, THEIR PREPARATION AND USE

CROSS REFERENCE TO RELATED APPLICATIONS

This application claims the benefit of U.S. Provisional Application No. 62/471,484, filed Mar. 15, 2017, the entirety of which is incorporated by reference herein.

BACKGROUND OF THE INVENTION

Tetrabenazine (NITOMAN™, XENAZINE™, Ro 1-9569), 1,3,4,6,7,11b-Hexahydro-9,10-dimethoxy-3-(2-methylpropyl)-2H-benzo[a]quinoline, is a vesicular monoamine transporter 2 (VMAT2) inhibitor. Tetrabenazine is commonly prescribed for the treatment of Huntington's disease (Savani et al., Neurology 2007, 68(10), 797; and Kenney et al., Expert Review of Neurotherapeutics 2006, 6(1), 7-17).

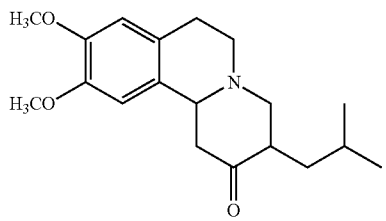

Tetrabenazine $d_6$-Tetrabenazine (USAN and INN: Deutetrabenazine) is a deuterated analog of tetrabenazine marketed in the United States under the tradename AUSTEDO®. It has improved pharmacokinetic properties when compared to the non-deuterated drug. See, e.g., U.S. Pat. No. 8,524,733.

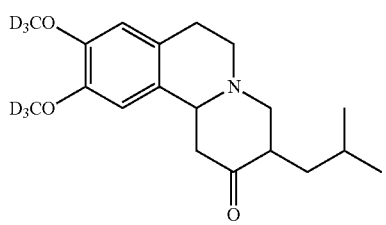

$d_6$-Tetrabenazine (Deutetrabenazine)

Processes of synthesis of deutetrabenazine are disclosed in U.S. Published Application No. 2015/0152099. Pharmaceutical compositions comprising deutetrabenazine are disclosed in U.S. Pat. No. 9,233,959. U.S. Published Application No. 2016/0287574 discloses deutetrabenazine for the treatment of abnormal involuntary movement disorders. Despite the desirable and beneficial effects of deutetrabenazine, there is a continuing need for high quality compositions to treat the aforementioned disorders.

To provide assurance that a drug product performs as intended, Applicants seeking marketing approval are required to summarize impurities identified in the drug product, both as produced using the proposed commercial manufacturing process, as well as after storage. Applicants must establish that the impurities are biologically safe at the levels identified in the drug product after manufacture and after storage. Drug products containing an acceptable impurity profile are needed.

BRIEF SUMMARY OF THE INVENTION

The disclosure is directed to pharmaceutical compositions comprising an admixture of a deutetrabenazine drug substance and a pharmaceutically acceptable carrier, wherein the deutetrabenazine drug substance comprises deutetrabenazine; 0.5 area-% or less of Compound 1, relative to the concentration of deutetrabenazine, based on a determination by an HPLC method; and 0.15 area-% or less of Compound 2, relative to the concentration of deutetrabenazine, based on a determination by the HPLC method; and wherein the pharmaceutical composition is stable when stored at room temperature for one to twenty-four months. The chemical structures of Compound 1 and Compound 2 are provided:

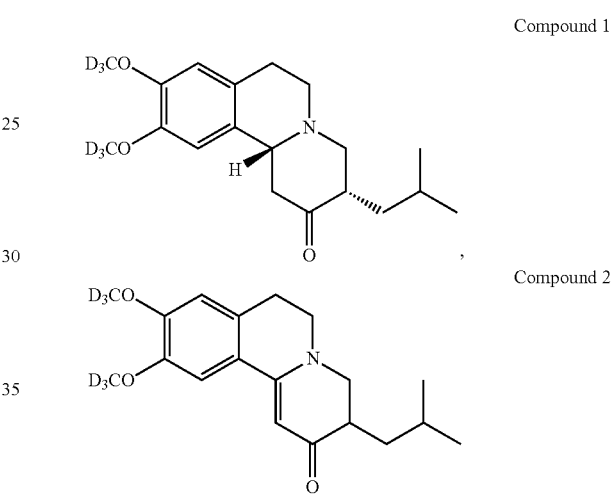

The disclosure is directed to isolated compounds having the structures of Compound 1 or Compound 2, and the salts and stereoisomers thereof:

Compositions comprising Compound 1 and/or Compound 2 are also described, as well as methods of using the compounds as reference standards.

The disclosure is also directed to processes for testing whether a sample of a composition comprising deutetrabenazine contains an undesirable impurity. Processes for producing a deutetrabenazine drug product are also described, as well as processes of distributing a deutetrabenazine drug product comprising a deutetrabenazine drug substance. Processes for validating a pharmaceutical product containing deutetrabenazine and a pharmaceutically acceptable carrier for distribution are described.

Methods of using the compounds and compositions described herein for treating subjects afflicted with a hyperkinetic movement disorder are also described.

BRIEF DESCRIPTION OF THE DRAWINGS

FIG. 1: FTIR Spectra of Compound 1.
FIG. 2: $^1$H NMR of Compound 1.
FIG. 3: $^{13}$C NMR of Compound 1.
FIG. 4: Representative Chromatogram of Compound 1.
FIG. 5: FTIR Spectra of Compound 2.
FIG. 6: $^1$H NMR of Compound 2.

FIG. 7: $^{13}$C NMR of Compound 2.

FIG. 8: Representative Chromatogram of Compound 2.

DETAILED DESCRIPTION OF THE INVENTION

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. In some aspects of the disclosure, "about" refers to a range of values that is ±10% of the recited value. For example, "about 10," refers to "9 to 11," as well as "10." The person skilled in the art will be able to interpret this as a matter of routine. In some cases, the number of significant figures used for a particular value may be one non-limiting method of determining the extent of the word "about". In other cases, the gradations used in a series of values may be used to determine the intended range available to the term "about" for each value. Where present, all ranges are inclusive and combinable. That is, references to values stated in ranges include every value within that range. It is understood that where a parameter range is provided, all integers within that range, and tenths thereof, are also provided by the invention. For example, "20-40 mg" includes 20.0 mg, 20.1 mg, 20.2 mg, 20.3 mg, etc. up to 40.0 mg.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The disclosure is directed to deutetrabenazine pharmaceutical compositions that are stable when stored at room temperature. In some aspects, the pharmaceutical compositions are stable when stored at room temperature for about one to about twenty-four months. In some aspects, the pharmaceutical compositions are stable when stored at room temperature for about one to about eighteen months. In some aspects, the pharmaceutical compositions are stable when stored at room temperature for about one to about twelve months. In some aspects, the pharmaceutical compositions are stable when stored at room temperature for about one to about six months. In some aspects, the pharmaceutical compositions are stable when stored at room temperature for about one to about three months. In some aspects, the pharmaceutical compositions are stable when stored at room temperature for about one month. For example, the pharmaceutical compositions of the disclosure are stable when stored at room temperature for about 1, 2, 3, 4, 5, 6, 7, 8, 9, 10, 11, 12, 13, 14, 15, 16, 17, 18, 19, 20, 21, 22, 23, or about 24 months.

The pharmaceutical compositions of the disclosure comprise an admixture of a deutetrabenazine drug substance and a pharmaceutically acceptable carrier. According to the disclosure, the deutetrabenazine drug substance comprises deutetrabenazine, Compound 1, and Compound 2. In particularly preferred aspects, the deutetrabenazine drug substance comprises deutetrabenazine, 0.5 area-% or less of Compound 1, relative to the concentration of deutetrabenazine, based on a determination by an HPLC method; and 0.15 area-% or less of Compound 2, relative to the concentration of deutetrabenazine, based on a determination by the HPLD method.

In preferred aspects, the deutetrabenazine drug substance, in addition to deutetrabenazine, comprises about 0.5 area-% or less of Compound 1, relative to the concentration of deutetrabenazine, based on a determination by an HPLC method. Exemplary HPLC methods are disclosed herein. In some aspects, the deutetrabenazine drug substance comprises about 0.1 area-% to about 0.5 area-% of Compound 1, relative to the concentration of deutetrabenazine, based on a determination by an HPLC method. In some aspects, the deutetrabenazine drug substance comprises about 0.1 area-% to about 0.4 area-% of Compound 1, relative to the concentration of deutetrabenazine, based on a determination by an HPLC method. In some aspects, the deutetrabenazine drug substance comprises about 0.1 area-% to about 0.3 area-% of Compound 1, relative to the concentration of deutetrabenazine, based on a determination by an HPLC method. In some aspects, the deutetrabenazine drug substance comprises about 0.1 area-% to about 0.2 area-% of Compound 1, relative to the concentration of deutetrabenazine, based on a determination by an HPLC method. In some aspects, the deutetrabenazine drug substance comprises about 0.1 area-% of Compound 1, relative to the concentration of deutetrabenazine, based on a determination by an HPLC method. In some aspects, the deutetrabenazine drug substance comprises about 0.15 area-% of Compound 1, relative to the concentration of deutetrabenazine, based on a determination by an HPLC method. In some aspects, the deutetrabenazine drug substance comprises about 0.2 area-% of Compound 1, relative to the concentration of deutetrabenazine, based on a determination by an HPLC method. In some aspects, the deutetrabenazine drug substance comprises about 0.25 area-% of Compound 1, relative to the concentration of deutetrabenazine, based on a determination by an HPLC method. In some aspects, the deutetrabenazine drug substance comprises about 0.3 area-% of Compound 1, relative to the concentration of deutetrabenazine, based on a determination by an HPLC method. In some aspects, the deutetrabenazine drug substance comprises about 0.35 area-% of Compound 1, relative to the concentration of deutetrabenazine, based on a determination by an HPLC method. In some aspects, the deutetrabenazine drug substance comprises about 0.4 area-% of Compound 1, relative to the concentration of deutetrabenazine, based on a determination by an HPLC method. In some aspects, the deutetrabenazine drug substance comprises about 0.45 area-% of Compound 1, relative to the concentration of deutetrabenazine, based on a determination by an HPLC method. In some aspects, the deutetrabenazine drug substance comprises about 0.5 area-% of Compound 1, relative to the concentration of deutetrabenazine, based on a determination by an HPLC method.

In preferred aspects, the deutetrabenazine drug substance, in addition to deutetrabenazine, comprises about 0.15 area-% or less of Compound 2, relative to the concentration of deutetrabenazine, based on a determination by an HPLC method. Exemplary HPLC methods are disclosed herein. In some aspects, the deutetrabenazine drug substance comprises about 0.05 area-% to about 0.15 area-% of Compound 2, relative to the concentration of deutetrabenazine, based on a determination by an HPLC method. In some aspects, the deutetrabenazine drug substance comprises about 0.05 area-% to about 0.1 area-% of Compound 2, relative to the concentration of deutetrabenazine, based on a determination by an HPLC method. In some aspects, the deutetrabenazine drug substance comprises about 0.15 area-% of Compound 2, relative to the concentration of deutetrabenazine, based on a determination by an HPLC method. In some aspects, the deutetrabenazine drug substance comprises about 0.1 area-% of Compound 2, relative to the concentration of deutetrabenazine, based on a determination by an HPLC method. In some aspects, the deutetrabenazine drug substance comprises about 0.05 area-% of Compound 2, relative to the concentration of deutetrabenazine, based on a determination by an HPLC method.

In some aspects, the pharmaceutical compositions of the disclosure comprise about 3 area-% or less of Compound 1, relative to the concentration of deutetrabenazine, based on a determination by an HPLC method. In other aspects, the pharmaceutical compositions of the disclosure comprise about 0.4 area-% or less of Compound 2, relative to the concentration of deutetrabenazine, based on a determination by an HPLC method. In yet other aspects, the pharmaceutical compositions of the disclosure comprise about 3 area-% or less of Compound 1 and about 0.4 area-% or less of Compound 2, each relative to the concentration of deutetrabenazine, based on a determination by an HPLC method.

In some aspects, the pharmaceutical compositions of the disclosure comprise 0.007 area-% to 3 area-% of Compound 1, relative to the concentration of deutetrabenazine, based on a determination by an HPLC method. In some aspects, the pharmaceutical compositions of the disclosure comprise 0.01 area-% to 3 area-% of Compound 1, relative to the concentration of deutetrabenazine, based on a determination by an HPLC method. In some aspects, the pharmaceutical compositions of the disclosure comprise 0.1 area-% to 3 area-% of Compound 1, relative to the concentration of deutetrabenazine, based on a determination by an HPLC method. In some aspects, the pharmaceutical compositions of the disclosure comprise 1 area-% to 3 area-% of Compound 1, relative to the concentration of deutetrabenazine, based on a determination by an HPLC method. For example, the pharmaceutical compositions of the disclosure comprise 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 area-% of Compound 1, relative to the concentration of deutetrabenazine, based on a determination by an HPLC method.

In some aspects, the pharmaceutical compositions of the disclosure comprise 0.007 area-% to 0.4 area-% of Compound 2, relative to the concentration of deutetrabenazine, based on a determination by an HPLC method. In some aspects, the pharmaceutical compositions of the disclosure comprise 0.03 area-% to 0.4 area-% of Compound 2, relative to the concentration of deutetrabenazine, based on a determination by an HPLC method. In some aspects, the pharmaceutical compositions of the disclosure comprise 0.1 area-% to 0.4 area-% of Compound 2, relative to the concentration of deutetrabenazine, based on a determination by an HPLC method. For example, the pharmaceutical compositions of the disclosure comprise 0.03, 0.04, 0.05, 0.06, 0.07, 0.08, 0.09, 0.1, 0.15, 0.2, 0.25, 0.3, 0.35, or 0.4 area-% of Compound 2, relative to the concentration of deutetrabenazine, based on a determination by an HPLC method.

According to the disclosure, pharmaceutical compositions of the disclosure include deutetrabenazine drug substances having a deuterium enrichment of no less than about 50%. In some aspects of the disclosure, pharmaceutical compositions of the disclosure include deutetrabenazine drug substances having deuterium enrichment of no less than about 90%. In some aspects, pharmaceutical compositions of the disclosure include deutetrabenazine drug substances having deuterium enrichment of no less than about 95%. In some aspects, pharmaceutical compositions of the disclosure include deutetrabenazine drug substances having deuterium enrichment of no less than about 98%.

In some aspects of the disclosure, the deutetrabenazine in the deutetrabenazine drug substances of the disclosure has a deuterium enrichment of no less than about 50%, at each of the methoxy moieties. In some aspects of the disclosure, the deutetrabenazine in the deutetrabenazine drug substances of the disclosure has a deuterium enrichment of no less than about 90%, at each of the methoxy moieties. In some aspects of the disclosure, the deutetrabenazine in the deutetrabenazine drug substances of the disclosure has a deuterium enrichment of no less than about 95%, at each of the methoxy moieties. In some aspects of the disclosure, the deutetrabenazine in the deutetrabenazine drug substances of the disclosure has a deuterium enrichment of no less than about 98%, at each of the methoxy moieties.

In some aspects of the disclosure, the Compound 1 in the deutetrabenazine drug substances of the disclosure has a deuterium enrichment of no less than about 50%, at each of the methoxy moieties. In some aspects of the disclosure, the Compound 1 in the deutetrabenazine drug substances of the disclosure has a deuterium enrichment of no less than about 90%, at each of the methoxy moieties. In some aspects of the disclosure, the Compound 1 in the deutetrabenazine drug substances of the disclosure has a deuterium enrichment of no less than about 95%, at each of the methoxy moieties. In some aspects of the disclosure, the Compound 1 in the deutetrabenazine drug substances of the disclosure has a deuterium enrichment of no less than about 98%, at each of the methoxy moieties.

In some aspects of the disclosure, the Compound 2 in the deutetrabenazine drug substances of the disclosure has a deuterium enrichment of no less than about 50%, at each of the methoxy moieties. In some aspects of the disclosure, the Compound 2 in the deutetrabenazine drug substances of the disclosure has a deuterium enrichment of no less than about 90%, at each of the methoxy moieties. In some aspects of the disclosure, the Compound 2 in the deutetrabenazine drug substances of the disclosure has a deuterium enrichment of no less than about 95%, at each of the methoxy moieties. In some aspects of the disclosure, the Compound 2 in the deutetrabenazine drug substances of the disclosure has a deuterium enrichment of no less than about 98%, at each of the methoxy moieties.

This disclosure is also directed to isolated compounds having the structures:

Compound 1

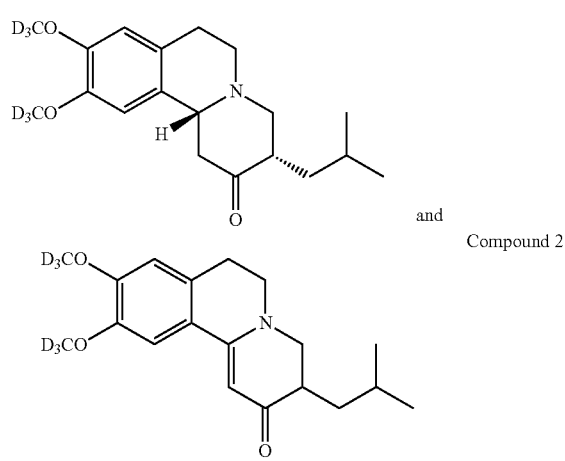

and

Compound 2 as well as the salts and stereoisomers thereof.

In an embodiment of the present invention, the isolated compound has the structure:

Compound 1

In an embodiment of the present invention, the isolated compound has the structure:

Compound 2

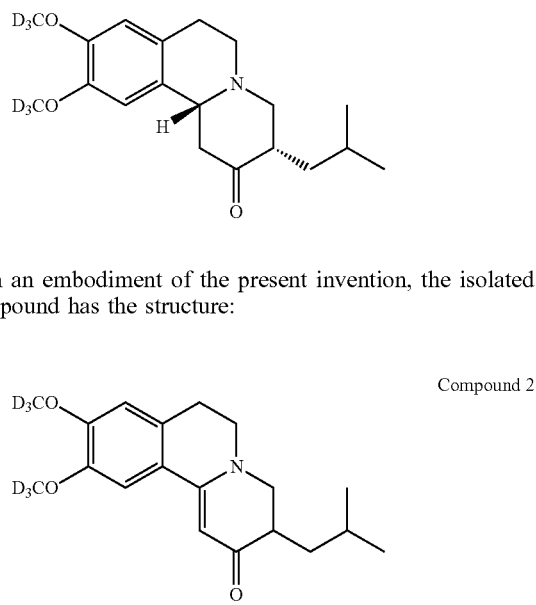

The invention further provides isolated Compounds 1 or 2, wherein each position represented as D has deuterium enrichment of no less than about 10%. Preferably, no less than about 50%. More preferably, no less than about 90%. Most preferably, no less than about 98%.

This invention also provides a composition comprising deutetrabenazine and at least one compound which has the structure:

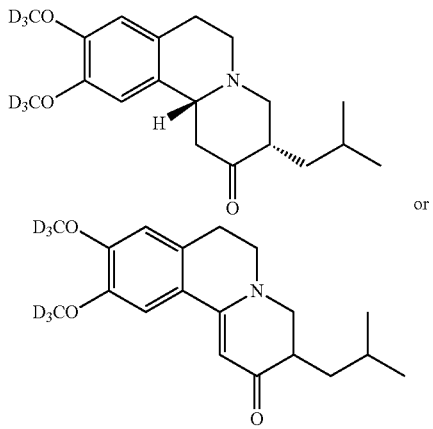

or wherein the ratio of the weight of the compound relative to the weight of the deutetrabenazine in the composition is from 99:1 to 1:99.

In an embodiment, the ratio of the weight of the compound relative to the weight of the deutetrabenazine in the composition is from 90:10 to 10:90 or from 85:15 to 15:85. For example, in some aspects, the ratio of the weight of the compound relative to the weight of the deutetrabenazine in the composition is 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, or 5:95. In other aspects, the ratio of the weight of the compound relative to the weight of the deutetrabenazine in the composition is 5:95, 10:90. 15:85, 20:80, 25:75, 30:70, 35:65, 40:60, 45:55, 50:50, 55:45, 60:40, 65:35, 70:30, 75:25, 88:20, 85:15, 90:10, or 95:5.

The disclosure also provides a composition comprising at least one compound having the structure:

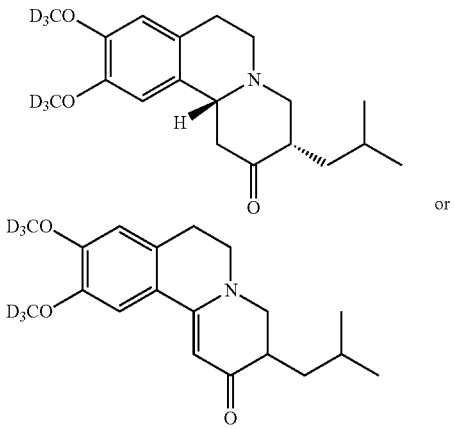

or wherein the composition is substantially free of deutetrabenazine. As used herein, "substantially free of deutetrabenazine" refers to having less than 1 wt. % of deutetrabenazine, preferably less than 0.1 wt. % of deutetrabenazine. As used herein, "free of deutetrabenazine" refers to having no amount of deutetrabenazine, as determined by an HPLC method.

Compound 1 is a diastereomer of deutetrabenazine. It can appear in the drug substance as a by-product of the manufacturing process. The amount of Compound 1 can increase over time, as the drug substance or drug product (pharmaceutical composition) is stored. According to the disclosure, in order to ensure stability over time in a pharmaceutical composition that will not contain more than 3 area-% of Compound 1, relative to the concentration of deutetrabenazine, based on a determination by an HPLC method, it has been determined that the deutetrabenazine drug substance used to prepare the pharmaceutical composition should have 0.5 area-% or less of Compound 1, relative to the concentration of deutetrabenazine, based on a determination by the HPLC method.

Compound 2 can form from the oxidation/dehydrogenation of deutetrabenazine. It can appear in the drug substance as a by-product of the manufacturing process. The amount of Compound 2 can increase over time, as the drug substance (pharmaceutical compositions) or drug product is stored. According to the disclosure, in order to ensure stability over time in a pharmaceutical composition that will not contain more than 0.4 area-% of Compound 2, relative to the concentration of deutetrabenazine, based on a determination by an HPLC method, it has been determined that the deutetrabenazine drug substance used to prepare the pharmaceutical composition should have 0.15 area-% or less of Compound 2, relative to the concentration of deutetrabenazine, based on a determination by the HPLC method.

According to the disclosure, in order to ensure stability over time in a pharmaceutical composition that will not contain more than 3 area-% of Compound 1 and 0.4 area-% of Compound 2, each relative to the concentration of deutetrabenazine, based on a determination by an HPLC method, the deutetrabenazine drug substance used to prepare the pharmaceutical composition should have 0.5 area-% or less of Compound 1 and 0.15 area-% or less of Compound 2, each relative to the concentration of deutetrabenazine, based on a determination by the HPLC method.

The disclosure also provides pharmaceutical compositions comprising an amount of deutetrabenazine and at least one of Compound 1 and Compound 2 wherein
a) Compound 1 is present in the pharmaceutical composition in an amount not more than 10 area-% relative to the concentration of deutetrabenazine, based on a determination by an HPLC method, or
b) Compound 2 is present in the pharmaceutical composition in an amount not more than 10 area-% relative to the concentration of deutetrabenazine, based on a determination by an HPLC method.

The disclosure also provides pharmaceutical compositions comprising an amount of deutetrabenazine and at least one of Compound 1 and Compound 2 wherein
a) Compound 1 is present in the pharmaceutical composition in an amount not more than 3 area-% relative to the concentration of deutetrabenazine, based on a determination by an HPLC method, or
b) Compound 2 is present in the pharmaceutical composition in an amount not more than 0.4 area-% relative to the concentration of deutetrabenazine, based on a determination by an HPLC method.

In one embodiment, at least one of Compound 1 and Compound 2 are present in the described pharmaceutical compositions.

In an embodiment, the pharmaceutical composition is in the form of a capsule, a tablet, or a liquid suspension. In another embodiment, the pharmaceutical composition is in an oral dosage unit form.

In an embodiment, the pharmaceutical composition comprises between 5-30 mg deutetrabenazine. In another embodiment, the pharmaceutical composition comprises between 6-24 mg deutetrabenazine. In another embodiment, the pharmaceutical composition comprises about 6 mg deutetrabenazine. In another embodiment, the pharmaceutical composition comprises about 9 mg deutetrabenazine. In another embodiment, the pharmaceutical composition comprises about 12 mg deutetrabenazine. In another embodiment the pharmaceutical composition comprises about 15 mg deutetrabenazine. In another embodiment, the pharmaceutical composition comprises about 18 mg deutetrabenazine. In another embodiment, the pharmaceutical composition comprises about 21 mg deutetrabenazine. In another embodiment, the pharmaceutical composition comprises about 24 mg deutetrabenazine.

In another embodiment, the pharmaceutical composition is prepared for once daily administration. In another embodiment, the pharmaceutical composition is prepared for more than once daily administration, for example, twice daily, three times daily, four times daily, etc.

The disclosure also provides a process for isolating Compound 1 comprising recrystallization of a mixture of deutetrabenazine and Compound 1 from ethanol to produce Compound 1.

The disclosure also provides a process for preparing Compound 2 comprising oxidation of deutetrabenazine to form Compound 2.

The disclosure also provides a process for testing whether a sample of a composition comprising deutetrabenazine contains an undesirable impurity, i.e., an undesirable amount of Compound 1 and/or Compound 2, which comprises the step of determining whether the sample contains a compound having the structure:

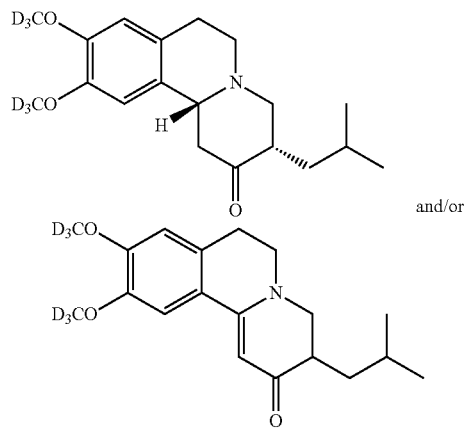

and/or

This invention also provides a process for producing a deutetrabenazine drug product comprising obtaining a deutetrabenazine drug substance and mixing the deutetrabenazine drug substance with suitable excipients so as to produce the deutetrabenazine drug product, wherein the deutetrabenazine drug substance comprises:
i) an amount of Compound 1 in the deutetrabenazine drug substance that is not more than 0.5 area-% Compound 1, relative to the concentration of deutetrabenazine, based on a determination by an HPLC method, or
ii) an amount of Compound 2 in the deutetrabenazine drug substance that is not more than 0.15 area-%

Compound 2, relative to the concentration of deutetrabenazine, based on a determination by an HPLC method.

In one embodiment, the process further comprises determining the amount of the at least one of Compound 1 and Compound 2 in the deutetrabenazine drug substance, based on a determination by an HPLC method.

This invention also provides a process for producing a deutetrabenazine drug product for commercial sale and/or human administration comprising obtaining a batch of deutetrabenazine drug product that comprises:
  i) an amount of Compound 1 in the batch of deutetrabenazine drug product that is not more than 3 area-% Compound 1, relative to the concentration of deutetrabenazine, based on a determination by an HPLC method, or
  ii) an amount of Compound 2 in the batch of deutetrabenazine drug product that is not more than 0.4 area-% Compound 2, relative to the concentration of deutetrabenazine, based on a determination by an HPLC method and
preparing the batch of deutetrabenazine drug product for commercial sale and/or human administration.

In one embodiment, the process further comprises determining the amount of the at least one of Compound 1 and Compound 2 in the deutetrabenazine drug product.

This invention also provides a process of distributing a deutetrabenazine drug product comprising a deutetrabenazine drug substance comprising:
  a) obtaining the deutetrabenazine drug product wherein the deutetrabenazine drug substance comprises:
    i) an amount of Compound 1 in the deutetrabenazine drug substance that is not more than 0.5 area-% Compound 1, relative to the concentration of deutetrabenazine, based on a determination by an HPLC method, or
    ii) an amount of Compound 2 in the deutetrabenazine drug substance that is not more than 0.15 area-% Compound 2, relative to the concentration of deutetrabenazine, based on a determination by an HPLC method; and
  b) distributing the deutetrabenazine drug product comprising the deutetrabenazine drug substance.

This invention also provides a process of distributing a deutetrabenazine drug product comprising,
  a) obtaining the deutetrabenazine drug product that comprises:
    i) an amount of Compound 1 in the deutetrabenazine drug product that is not more than 3 area-% Compound 1, relative to the concentration of deutetrabenazine, based on a determination by an HPLC method, or
    ii) an amount of Compound 2 in the deutetrabenazine drug product that is not more than 0.4 area-% Compound 2, relative to the concentration of deutetrabenazine, based on a determination by an HPLC method; and
  b) distributing the deutetrabenazine drug product.

This invention also provides an impurity for use, as a reference standard to detect trace amounts of the impurity in a pharmaceutical composition comprising deutetrabenazine, wherein the impurity is Compound 1 or Compound 2.

This invention also provides a method of determining the concentration of an impurity in a composition comprising deutetrabenazine, the method comprising:
  a) preparing a sample solution from the pharmaceutical composition,
  b) preparing a diluent solution comprising acetonitrile,
  c) preparing a standard solution comprising deutetrabenazine and the diluent solution,
  d) preparing a resolution solution comprising deutetrabenazine and the impurity,
  e) preparing a buffer solution by dissolving 770 mg of ammonium acetate in 1000 mL of water,
  f) injecting into the HPLC the diluent solution, the resolution solution, the standard solution, and the sample solution,
  g) running the HPLC using ultraviolet absorption at 190-400 nm (preferably 220 nm) of the buffer solution and diluent as the mobile phase with a gradient program started with 80% buffer/20 diluent and ramp up to 100% buffer over 20 mins,
  h) determining the retention time (RT) and the areas of the peaks of the impurity in the chromatograms of the sample solution, and
  i) performing quantitation of the impurity with respect to the corresponding peaks in the chromatograms of the sample solution,
wherein the impurity is Compound 1 or Compound 2.

This invention also provides a method of determining the concentration of an impurity in a pharmaceutical composition comprising deutetrabenazine and a pharmaceutically acceptable carrier, the method comprising,
  a) preparing a sample solution from the pharmaceutical composition,
  b) preparing a diluent solution comprising isopropyl alcohol and acetonitrile,
  c) preparing a standard solution comprising deutetrabenazine and the diluent solution,
  d) preparing a resolution solution comprising deutetrabenazine and the impurity,
  e) preparing a buffer solution by dissolving ammonium acetate in water,
  f) injecting into the HPLC the diluent solution, the resolution solution, the standard solution, and the sample solution,
  g) running the HPLC using ultraviolet absorption at 190-400 nm or 220 nm and a mixture of the buffer solution and acetonitrile as the mobile phase,
  h) determining the retention time (RT) and the areas of the peaks of the impurity in the chromatograms of the sample solution, and
  i) performing quantitation of the impurity with respect to the corresponding peaks in the chromatograms of the sample solution,
wherein the impurity is Compound 1 or Compound 2.

This invention also provides a method of treating a subject afflicted with a hyperkinetic movement disorder comprising administering to the subject a pharmaceutical composition of the invention.

This invention also provides a method of treating a subject afflicted with Huntington's disease comprising administering to the subject a pharmaceutical composition of the invention.

This invention also provides a method of treating a subject afflicted with chorea related to Huntington's disease comprising administering to the subject a pharmaceutical composition of the invention.

This invention also provides a method of treating a subject afflicted with tardive dyskinesia comprising administering to the subject a pharmaceutical composition of the invention.

This invention also provides a method of treating a subject afflicted with a tic associated with Tourette syndrome, comprising administering to the subject a pharmaceutical composition of the invention.

This invention also provides a process for validating a batch of a pharmaceutical product containing deutetrabenazine and a pharmaceutically acceptable carrier for distribution comprising:
a) determining the amount of at least one of Compound 1 and Compound 2 based on a determination by an HPLC method; and
b) validating the batch for distribution only if
  i) the batch is determined to have not more than 3 area-% Compound 1, relative to the concentration of deutetrabenazine, based on a determination by an HPLC method or
  ii) the batch is determined to have not more than 0.4 area-% Compound 2, relative to the concentration of deutetrabenazine, based on a determination by an HPLC method.

This invention also provides a process for preparing a validated pharmaceutical composition comprising deutetrabenazine comprising:
a) obtaining a batch of deutetrabenazine drug substance;
b) determining the amount of at least one of Compound 1 and Compound 2, based on a determination by an HPLC method; and
c) preparing the pharmaceutical composition from the batch only if
  i) the batch is determined to have not more than 0.5% Compound 1, relative to the concentration of deutetrabenazine, based on a determination by an HPLC method or
  ii) the batch is determined to have not more than 0.15% Compound 2, relative to the concentration of deutetrabenazine, based on a determination by an HPLC method.

Each embodiment disclosed herein is contemplated as being applicable to each of the other disclosed embodiments. Thus, all combinations of the various elements described herein are within the scope of the invention.

For example, the elements recited in the packaging and pharmaceutical composition embodiments can be used in the method and use embodiments described herein.

Terms

As used herein, and unless stated otherwise, each of the following terms shall have the definition set forth below.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The terms "3S,11bS enantiomer" or the term "3R,11bR enantiomer" refers to either of the deutetrabenazine stereoisomers having the structural formulas shown below:

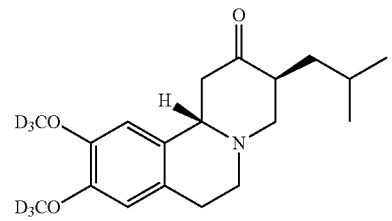

(3S, 11bS)-enantiomer

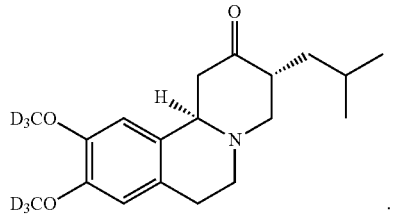

(3R, 11bR)-enantiomer

In certain embodiments, a chemical structure may be drawn as either the 3S,11bS enantiomer or the 3R,11bR enantiomer, but the text of the specification may indicate that the 3S,11bS enantiomer, the 3R,11bR enantiomer, a racemic mixture thereof (which may be described as (RR, SS)-d6-tetrabenazine), or all of the foregoing may be intended to be described.

As used herein, "drug substance" refers to the active ingredient in a drug product or to the composition containing the active ingredient before it is formulated into in a drug product, which provides pharmacological activity or other direct effect in the diagnosis, cure, mitigation, treatment, or prevention of disease, or to affect the structure or any function of the body of man or animals.

As used herein, "drug product" refers to the formulated or finished dosage form containing the drug substance as well as at least one pharmaceutically acceptable carrier.

As used herein, an "isolated" compound is a compound isolated from the crude reaction mixture following an affirmative act of isolation. The act of isolation involves separating the compound from the other known components of the crude reaction mixture, with some impurities, unknown side products and residual amounts of the other known components of the crude reaction mixture permitted to remain. Purification is an example of an affirmative act of isolation.

As used herein, the term "stable," in reference to deutetrabenazine, means deutetrabenazine wherein the level of a specific impurity (for example, Compound 1, Compound 2, or a combination thereof) does not increase to more than a specific limit, when maintained at a specific temperature for a specific period of time. More specifically, the term "stable" means deutetrabenazine wherein the level of Compound 1, does not increase to more than 3% of the total amount of deutetrabenazine area as measured by HPLC, or wherein the level of Compound 2, does not increase to more than 0.4% of the total amount of deutetrabenazine area as measured by HPLC, when maintained at room temperature, for about 1 to about 24 months.

As used herein, "room temperature" refers to a temperature ranging from about 20° C. to about 30° C.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R § 211.166, the entire content of which is hereby incorporated by reference.

As used herein, "approximately" in the context of a numerical value or range means±5% of the numerical value or range recited or claimed.

As used herein, an "amount" of a compound as measured in milligrams refers to the milligrams of compound present in a preparation, regardless of the form of the preparation. An "amount of compound which is 40 mg" means the amount of the compound in a preparation is 40 mg, regardless of the form of the preparation. Thus, when in the form with a carrier, the weight of the carrier necessary to provide a dose of 40 mg compound would be greater than 40 mg due to the presence of the carrier.

As used herein, "treating" and "treatment" encompasses, e.g., inducing inhibition, regression, or stasis of a disease, disorder or condition, or ameliorating or alleviating a symptom of a disease, disorder or condition. "Ameliorating" or "alleviating" a condition or state as used herein shall mean to relieve or lessen the symptoms of that condition or state. "Inhibition" of disease progression or disease complication in a subject as used herein means preventing or reducing the disease progression and/or disease complication in the subject.

"Administering to the subject" means the giving of, dispensing of, or application of medicines, drugs, or remedies to a subject to relieve, cure, or reduce the symptoms associated with a condition, e.g., a pathological condition.

The drug substance of the present invention, e.g., deutetrabenazine, may be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. Capsules or tablets may contain suitable binders, lubricants, disintegrating agents, diluents, coloring agents, flow-inducing agents, and melting agents.

A dosage unit of the compounds used in the method of the present invention may comprise a single compound or mixtures thereof with additional therapeutic agents.

A "dose" or "dosage unit" or "unit dosage" of deutetrabenazine as measured in milligrams refers to the milligrams of deutetrabenazine present in a preparation, regardless of the form of the preparation. A dosage unit may comprise a single compound or mixtures of compounds thereof. A dosage unit can be prepared for oral dosage forms, such as tablets, capsules, pills, powders, liquid suspensions, and granules. For example, the "dose" or "dosage unit" of deutetrabenazine may be 6, 9, 12, 15, 18, 21 or 24 mg.

As used herein, a "pharmaceutically acceptable" component is one that is suitable for use with humans and/or animals without undue adverse side effects (such as toxicity, irritation, and allergic response) commensurate with a reasonable benefit/risk ratio.

The subject invention is also intended to include all isotopes of atoms occurring on the compounds disclosed herein, including impurities. Isotopes include those atoms having the same atomic number but different mass numbers. By way of general example and without limitation, isotopes of hydrogen include tritium and deuterium. Isotopes of carbon include C-12, C-13, and C-14.

As used herein, "detection limit" for an analytical method used in screening or testing for the presence of a compound in a sample is a threshold under which the compound in a sample cannot be detected by the analytical method used. The detection limits of a given HPLC method for detecting an impurity in a sample containing of deutetrabenazine may vary based on the method and the impurity or impurities being detected. For example, the detection limit of the typical HPLC method for detecting Compound 1 is 0.01 area-% and the detecting limit for detecting Compound 2 is 0.03 area-%.

As used herein, "quantitation limit" for an analytical method used in screening or testing for the presence of a compound in a sample is a threshold under which the compound in a sample cannot be quantified by the analytical method used. The quantitation limits of a given HPLC method for detecting an impurity in a sample containing of deutetrabenazine may vary based on the impurity or impurities being detected. For example, the quantitation limit of the typical HPLC method for quantifying Compound 1 is 0.007 area-% and the quantitation limit for Compound 2 is 0.007 area-%.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography, elemental analysis, Ames test, dissolution, stability and any other quality that can be determined by an analytical method. Once the characteristics of a compound are known, the information can be used to, for example, screen or test for the presence of the compound in a sample.

As used herein, "NMT" means no more than. As used herein, "LT" means less than.

The amount of impurities is measured by reverse phase HPLC unless otherwise specified.

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention, i.e. a therapeutically effective amount. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "preparing drug product for commercial sale" means an activity undertaken in preparation for commercial sale. Examples include, but are not limited to, coloring, coding, stamping, packaging the drug product.

As used herein, "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

As used herein, "is/are deuterium," when used to describe a given position in a molecule or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

Table 1 shows the structures of Compounds 1-2.

TABLE 1

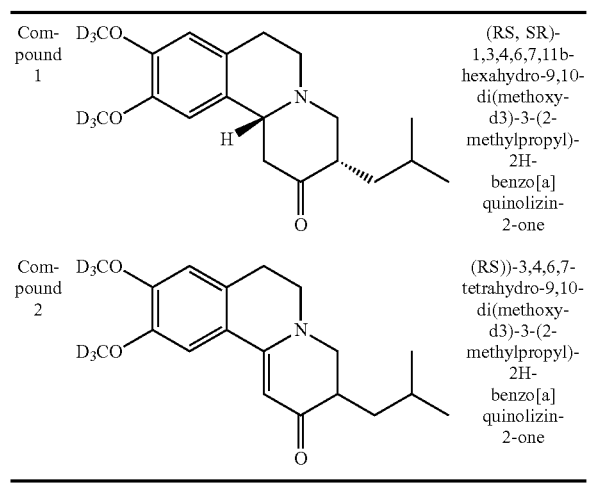

| Compound 1 | (RS, SR)-1,3,4,6,7,11b-hexahydro-9,10-di(methoxy-d3)-3-(2-methylpropyl)-2H-benzo[a]quinolizin-2-one |
| Compound 2 | (RS))-3,4,6,7-tetrahydro-9,10-di(methoxy-d3)-3-(2-methylpropyl)-2H-benzo[a]quinolizin-2-one |

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Examples

Example 1—Preparation of Compound 1

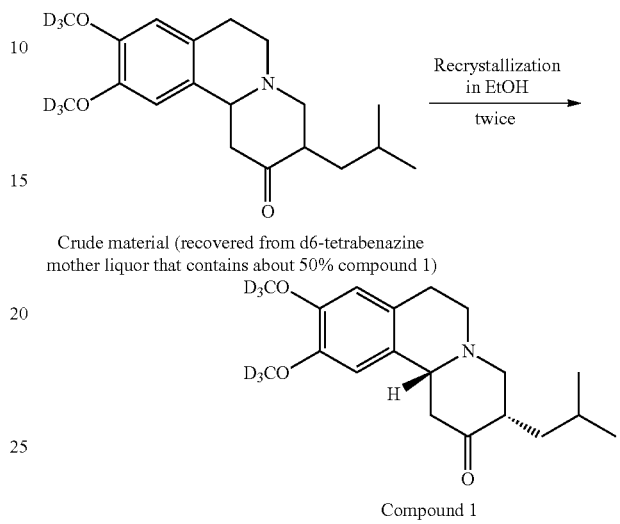

The crude material (10 g) which was obtained from mother liquor of deutetrabenazine was purified by recrystallization with EtOH (2×3V) to give 2.5 g of compound 1 as an off white solid.

NMR Identity Analysis of Compound 1

Compound 1:

The following data in Table 2 was determined using a sample of Compound 1, in CDCl$_3$ (99.9 atom % D), using a 300 MHz NMR instrument. See FIGS. 2 and 3.

TABLE 2

Assignment of $^1$H NMR and $^{13}$C NMR$^{a,c}$

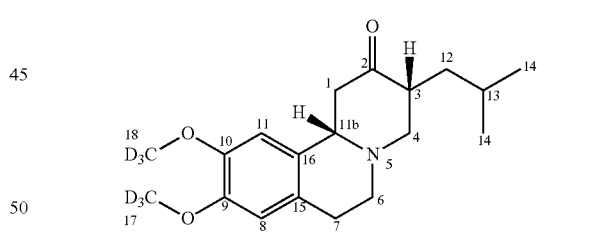

| Position | $^1$H chemical shift (split pattern, coupling constant) |
|---|---|
| 1 | 2.61 (m, 1H), 2.84 (m, 1H), |
| 2 | N/A |
| 3 | 2.53 (m, 1H) |
| 4 | 2.71 (m, 1H), 2.98 (m, 1H) |
| 5 | N/A |
| 6 | 2.53 (m, 2H), 3.02 (m, 2H) |
| 7 | 3.14 (m, 1H), 2.65 (m, 1H) |
| 8 | 6.56 (s, 1H) |
| 9 | N/A |
| 10 | N/A |
| 11 | 6.61 (s, 1H) |
| 11b | 3.42 (d, J = 10.8 Hz, 1H) |
| 12 | 1.54 (m, 1H), 1.80 (M, 1H) |
| 13 | 1.55 (m, 1H) |
| 14 | 0.92 (m, 6H) |

TABLE 2-continued

Assignment of $^1$H NMR and $^{13}$C NMR$^{a,c}$

| Position | $^{13}$C chemical shift (split pattern, coupling constant) |
|---|---|
| 15 | N/A |
| 16 | N/A |
| 17 | N/A |
| 18 | N/A |
| N/A | N/A |

| Position | $^{13}$C chemical shift (split pattern, coupling constant) |
|---|---|
| 1 | 45.22 (s) |
| 2 | 212.42 (s) |
| 3 | 49.06 (s) |
| 4 | 59.66 (s) |
| 5 | N/A |
| 6 | 51.62 (s) |
| 7 | 29.19 (s) |
| 8 | 107.64 (s) |
| 9 | 147.67 (s) |
| 10 | 147.43 (s) |
| 11 | 111.40 (s) |
| 11b | 62.01 (s) |
| 12 | 40.54 (s) |
| 13 | 25.74 (s) |
| 14 | 22.71 (d) |
| 15 | 128.67 (s) |
| 16 | 126.43 (s) |
| 17 | N/A |
| 18 | N/A |
| N/A | N/A |

$^a$The assignment is based on the chemical shifts and 1H-13C couplings extracted from HSQC (Heteronuclear Single Quantum Coherence Spectroscopy) and HMBC (Heteronuclear Multiple Bond Correlation) experiments.
$^b$Spectra is calibrated peak by reference to the NMR solvent peak.

Example 2—Preparation of Compound 2

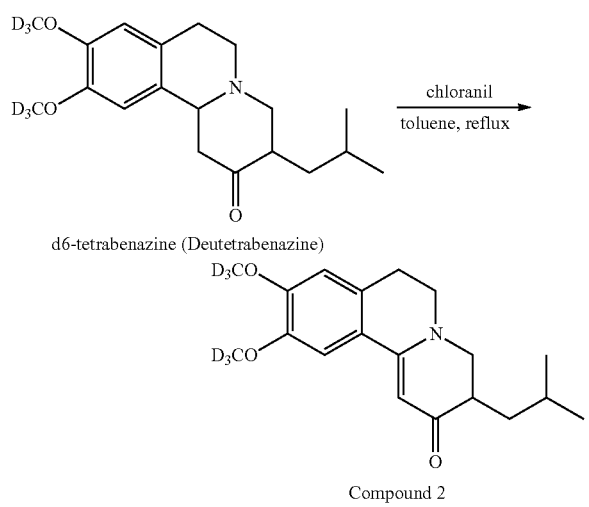

To deutetrabenazine (31.7 g, 10.0 mmol) and chloranil (26 g, 10.5 mmol) was added toluene (300 mL), and the mixture was heated at reflux for 2.5 h. To the dark solution was added toluene (500 mL) and the mixture was washed with 300 mL of 2 N NaOH and $H_2O$. The toluene solution was dried ($Na_2SO_4$), filtered, and evaporated to dryness. The residue was crystallized from ethyl acetate to give 21 g (66%) of Compound 2 as off-white crystalline solid.

NMR Identity Analysis of Compound 2
Compound 2:
The following data in Table 3 was determined using a sample of Compound 2, in $CDCl_3$ (99.9 atom % D), using a 300 MHz NMR instrument.

TABLE 3

Assignment of $^1$H NMR and $^{13}$C NMR$^{a,b}$

| Position | $^1$H chemical shift (split pattern, coupling constant) |
|---|---|
| 1 | 5.67 (s, 1H) |
| 2 | N/A |
| 3 | 2.47 (m, 1H) |
| 4 | 3.66 (dd, J = 5.4 Hz, J = 12.6 Hz, 1H) |
|   | 3.32 (dd, J = 8.7 Hz, J = 12.3 Hz, 1H) |
| 5 | N/A |
| 6 | 3.40 (m, 1H) |
| 7 | 2.96 (m, 1H) |
| 8 | 6.67 (s, 1H) |
| 9 | N/A |
| 10 | N/A |
| 11 | 7.17 (s, 1H) |
| 11b | N/A |
| 12 | 1.32 (m, 1H) |
|   | 1.73 (m, 1H) |
| 13 | 1.72 (m, 1H) |
| 14 | 0.92 (m, 6H) |
| 15 | N/A |
| 16 | N/A |
| 17 | N/A |
| 18 | N/A |
| N/A | N/A |

| Position | $^{13}$C chemical shift (split pattern) |
|---|---|
| 1 | 94.09 (s) |
| 2 | 195.29 (s) |
| 3 | 41.95 (s) |
| 4 | 55.71 (d) |
| 5 | N/A |
| 6 | 48.97 (s) |
| 7 | 28.37 (s) |
| 8 | 110.35 (s) |
| 9 | 156.46 (s) |
| 10 | 151.40 (s) |
| 11 | 108.16 (s) |
| 11b | 120.68 (s) |
| 12 | 37.42 (s) |
| 13 | 25.43 (s) |
| 14 | 23.45 (d) |
| 15 | 147.92 (s) |
| 16 | 128.91 (s) |
| 17 | N/A |
| 18 | N/A |
| N/A | N/A |

$^a$The assignment is based on the coupling pattern of the signals, coupling constants and chemical shifts.

TABLE 3-continued

Assignment of $^1$H NMR and $^13$C NMR$^{a,b}$ $^b$Spectra is calibrated by reference to the NMR solvent peak.
See FIGS. 6 and 7

Example 3—Preparation of Crude Deutetrabenazine

Step 1:
2-acetyl-N,N,N,4-tetramethyl-1-pentanaminium iodide

3-[(dimethylamino)methyl]-5-methyl-hexan-2-one (90 g, 0.526 mol, 1.00 eq) was charged with methyl tert-butyl ether (1.35 L, 15.0 vol) and cooled 0-10° C. Methyl iodide (171 g, 1.209 mol, 2.3 eq) was added slowly to the reaction mixture and stirred for 15 hours at 25-35° C. The reaction was warmed to 35-40° C. for 2 hours. The precipitated solid was filtered under nitrogen and was washed with methyl tert-butyl ether (900 mL, 10.0 vol). The crude product was further purified by slurrying in ethyl acetate (1.46 L, 10 vol) and filtered to give 2-acetyl-N,N,N,4-tetramethyl-1-pentanaminium iodide (146 g) as a white solid.

Step 2:

2-acetyl-N,N,N,4-tetramethyl-1-pentanaminium iodide is charged to a suspension containing $d_6$-6,7-dimethoxy-3,4-dihydroisoquinoline (hydrochloride or freebase, 1.00 eq) and solvent. (If $d_6$-6,7-dimethoxy-3, 4-dihydroisoquinoline hydrochloride is used, a base is added to the reaction mixture at room temperature.) The reaction mixture is stirred at the appropriate temperature, cooled, and water is added. The reaction mass is filtered and the solids are washed with water and dried to afford the product.

Example 4—Analysis of the Amounts of Compounds 1 and 2 in a Sample of Deutetrabenazine Drug Substance Compounds 1 and 2 are useful to determine the purity of a deutetrabenazine containing composition. See FIGS. 4 and 8

TABLE 4

| Apparatus | |
|---|---|
| Instrument | High pressure liquid chromatography |
| Detector | PDA/UV detector |
| Column | X-Bridge, C18, 150 × 4.6 mm, 3.5 μm or Equivalent |
| Wavelength | 220 nm |
| Injection volume | 10.0 μL |
| Column oven temperature | 30° C. |
| Flow rate | 1.0 mL/min |
| Run time | 25 min |

Mobile phase A: 10 mM Ammonium Acetate aqueous solution
Mobile phase B: Acetonitrile
Diluent: Acetonitrile

TABLE 5

| Gradient program: | | | |
|---|---|---|---|
| Time (min) | Flow (mg/mL) | Mobile phase—A % | Mobile phase—B % |
| 0.01 | 1.0 | 80 | 20 |
| 8.0 | 1.0 | 50 | 50 |
| 18.0 | 1.0 | 0 | 100 |
| 20.0 | 1.0 | 0 | 100 |
| 20.1 | 1.0 | 80 | 20 |
| 25.0 | 1.0 | 80 | 20 |

TABLE 6

Retention time and Relative retention time for determination of related substances:

| Name | RT (mm) | RRT |
|---|---|---|
| Deutetrabenazine | 13.16 | 1.00 |
| Compound 1 | 14.25 | 1.08 |
| Compound 2 | 9.94 | 0.76 |

Example 4: Fourier Transform Infrared Spectroscopic (FTIR) Analysis

FTIR spectra of Compounds 1 and 2 are depicted in FIGS. 1 and 5.

Example 4—Long Term Stability in Deutetrabenazine Drug Product

TABLE 7

| 7.5 mg tablets stored at room temperature | | | | | | | |
|---|---|---|---|---|---|---|---|
| Attribute | T = 0 | 1 month | 3 month | 6 month | 9 month | 12 month | 18 month | 24 month |
| Assay | 101.1 | 99.6 | 100.3 | 95.6 | 102.3 | 102.9 | 104.0 | 99.7 |
| Compound 1 | 0.29 | 0.40 | 0.40 | 0.50 | 0.54 | 0.53 | 0.52 | 0.49 |
| Compound 2 | 0.17 | 0.19 | 0.18 | 0.20 | 0.22 | 0.28 | 0.25 | 0.24 |

TABLE 8

| | | | | 15 mg tablets stored at room temperature | | | | |
|---|---|---|---|---|---|---|---|---|
| Attribute | T = 0 | 1 month | 3 month | 6 month | 9 month | 12 month | 18 month | 24 month |
| Assay | 94.8 | 101.3 | 97.1 | 99.3 | 101.0 | 99.6 | 99.8 | 105.3 |
| Compound 1 | 0.14 | 0.25 | 0.33 | 0.31 | 0.31 | 0.24 | 0.25 | 0.25 |
| Compound 2 | 0.22 | 0.19 | 0.34 | 0.17 | 0.17 | 0.18 | 0.20 | 0.19 |

Example 5

A 90-day GLP general rat toxicology study was conducted with Compound 1. In that study, the no observed adverse effect level (NOAEL) dose for deutetrabenazine was 10 mg/kg/day. Those doses were shown to provide 0.346 mg of Compound 1/kg/day in rats, which approximates a human equivalent dose of 0.056 mg/kg.

Example 6

A 3-day GLP mouse micronucleus study was conducted with Compound 1. That study included a GLP Bacterial Reverse Mutation Assay of deutetrabenazine with Compound 1. That study also included an in vitro Chromosome Aberration Test in Cultured Human Peripheral Blood Lymphocytes. In the study, the highest level of 80 mg/kg/day of deutetrabenazine was not genotoxic in males and females. That dose level was predicted to provide 2.77 mg Compound 1/kg/day in mice, which approximates to a human equivalent dose of 0.23 mg/kg.

ASPECTS

Aspect 1. An isolated compound having the structure:

Compound 1

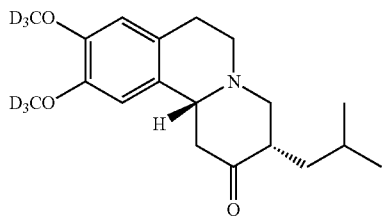

or

Compound 2

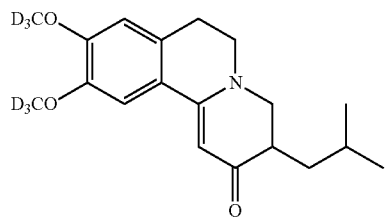

or a salt or stereoisomer thereof.

Aspect 2. The isolated compound of Aspect 1, which has the structure:

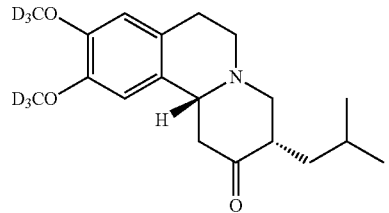

or a salt or stereoisomer thereof.

Aspect 3. The isolated compound of Aspect 1, which has the structure:

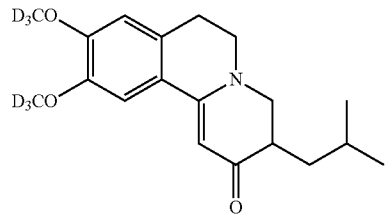

or a salt or stereoisomer thereof.

Aspect 4. A composition comprising deutetrabenazine and at least one compound which has the structure:

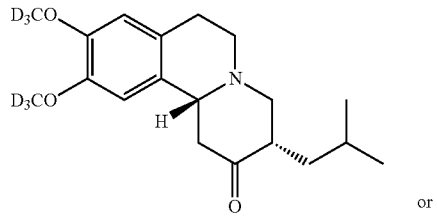

or

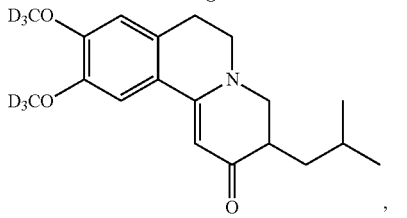

wherein the ratio of the weight of the compound relative to the weight of the deutetrabenazine. in the composition is from 99:1 to 1:99.

Aspect 5. A composition comprising a compound having the structure:

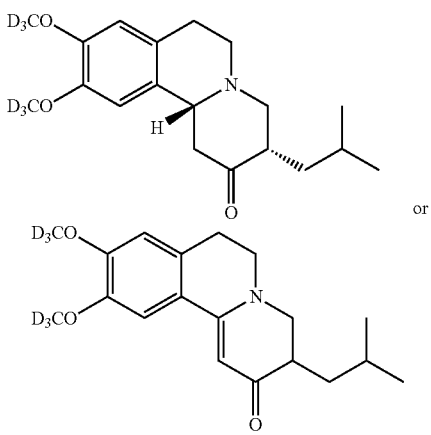

wherein the composition is substantially free of deutetrabenazine.

Aspect 6. The composition of any one of Aspects 4 or 5, wherein the compound has the structure:

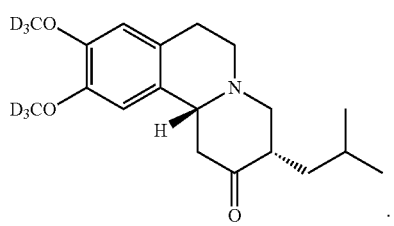

Aspect 7. The composition of any one of Aspects 4 or 5, wherein the compound has the structure:

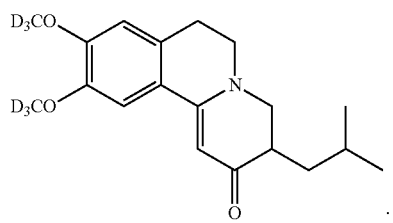

Aspect 8. A pharmaceutical composition comprising an amount of deutetrabenazine and at least one of Compound 1 and Compound 2 wherein
 a) Compound 1 is present in the pharmaceutical composition in an amount not more than 10 area-% relative to the concentration of deutetrabenazine, based on a determination by an HPLC method, or
 b) Compound 2 is present in the pharmaceutical composition in an amount not more than 10 area-% relative to the concentration of deutetrabenazine, based on a determination by an HPLC method.

Aspect 9. The pharmaceutical composition of Aspect 8, wherein
 a) Compound 1 is present in the pharmaceutical composition in an amount not more than 3 area-% relative to the concentration of deutetrabenazine, based on a determination by an HPLC method, or
 b) Compound 2 is present in the pharmaceutical composition in an amount not more than 0.4 area-% relative to the concentration of deutetrabenazine, based on a determination by an HPLC method.

Aspect 10. The pharmaceutical composition of Aspect 9, wherein
 a) Compound 1 is present in the pharmaceutical composition in an amount not more than 0.15 area-% relative to the concentration of deutetrabenazine, based on a determination by an HPLC method, or
 b) Compound 2 is present in the pharmaceutical composition in an amount not more than 0.15 area-% relative to the concentration of deutetrabenazine, based on a determination by an HPLC method.

Aspect 11. The pharmaceutical composition of Aspect 9, wherein
 a) Compound 1 is present in the pharmaceutical composition in an amount greater than 0.01 area-%, and not more than 3 area-% relative to the concentration of deutetrabenazine, based on a determination by an HPLC method, or
 b) Compound 2 is present in the pharmaceutical composition in an amount greater than 0.01 area-%, and not more than 0.4 area-%, relative to the concentration of deutetrabenazine, based on a determination by an HPLC method.

Aspect 12. The pharmaceutical composition of Aspect 9, wherein
 a) Compound 1 is present in the pharmaceutical composition in an amount greater than 0.01 area-%, and not more than 0.15 area-% relative to the concentration of deutetrabenazine, based on a determination by an HPLC method, or
 a) Compound 2 is present in the pharmaceutical composition in an amount greater than 0.01 area-%, and not more than 0.15 area-%, relative to the concentration of deutetrabenazine, based on a determination by an HPLC method.

Aspect 13. The pharmaceutical composition of any one of Aspects 11-12, wherein
 a) Compound 1 is present in the pharmaceutical composition in an amount less than 0.04 area-% relative to the concentration of deutetrabenazine, based on a determination by an HPLC method, or
 b) Compound 2 is present in the pharmaceutical composition in an amount less than 0.04 area %, relative to the concentration of deutetrabenazine, based on a determination by an HPLC method.

Aspect 14. The pharmaceutical composition of Aspect 9, wherein
 a) Compound 1 is present in the pharmaceutical composition in an amount less than 0.01 area-% relative to the concentration of deutetrabenazine, based on a determination by an HPLC method, or
 b) Compound 2 is present in the pharmaceutical composition in an amount less than 0.01 area-% relative to the concentration of deutetrabenazine, based on a determination by an HPLC method.

Aspect 15. The pharmaceutical composition of any one of Aspects 8-14, comprising Compound 1 and Compound 2.

Aspect 16. The pharmaceutical composition of any one of Aspects 8-14, comprising Compound 1.

Aspect 17. The pharmaceutical composition of any one of Aspects 8-14, comprising Compound 2.

Aspect 18. The pharmaceutical composition of any one of Aspects 8-17, comprising deutetrabenazine.

Aspect 19. The pharmaceutical composition of any one of Aspects 8-18, in the form of a capsule, a tablet, or a liquid suspension.

Aspect 20. The pharmaceutical composition of Aspect 19, in an oral dosage unit form.

Aspect 21. The pharmaceutical composition of Aspect 20, comprising between 5-30 mg deutetrabenazine.

Aspect 22. The pharmaceutical composition of Aspect 21, comprising between 6-24 mg deutetrabenazine.

Aspect 23. The pharmaceutical composition of Aspect 22, comprising about 6 mg deutetrabenazine.

Aspect 24. The pharmaceutical composition of Aspect 22, comprising about 9 mg deutetrabenazine.

Aspect 25. The pharmaceutical composition of Aspect 22, comprising about 12 mg deutetrabenazine.

Aspect 26. The pharmaceutical composition of Aspect 22, comprising about 15 mg deutetrabenazine.

Aspect 27. The pharmaceutical composition of Aspect 22, comprising about 18 mg deutetrabenazine.

Aspect 28. The pharmaceutical composition of Aspect 22, comprising about 21 mg deutetrabenazine.

Aspect 29. The pharmaceutical composition of Aspect 22, comprising about 24 mg deutetrabenazine.

Aspect 30. The pharmaceutical composition of Aspect 22, prepared for once daily administration.

Aspect 31. The pharmaceutical composition of Aspect 22, prepared for more than once daily administration.

Aspect 32. A process for testing whether a sample of a composition comprising deutetrabenazine contains an undesirable impurity which comprises the step of determining whether the sample contains at least one compound having the structure:

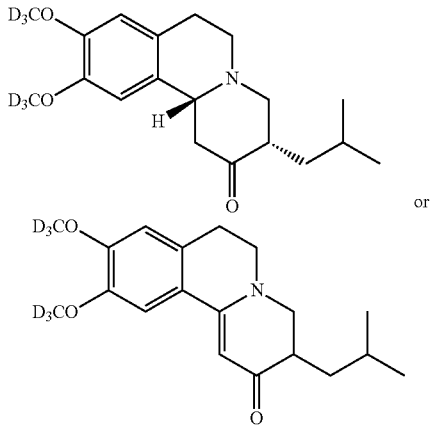

based on a determination by an HPLC method.

Aspect 33. A process for producing a deutetrabenazine drug product comprising obtaining a deutetrabenazine drug substance and mixing the deutetrabenazine drug substance with suitable excipients so as to produce the deutetrabenazine drug product, wherein the deutetrabenazine drug substance comprises:
i) an amount of Compound 1 in the deutetrabenazine drug substance that is not more than 0.5 area-% Compound 1, relative to the concentration of deutetrabenazine, based on a determination by an HPLC method or
ii) an amount of Compound 2 in the deutetrabenazine drug substance that is not more than 0.15 area-% Compound 2, relative to the concentration of deutetrabenazine, based on a determination by an HPLC method.

Aspect 34. The process of Aspect 33, wherein the process further comprises determining the amount of the at least one of Compound 1 and Compound 2 in the deutetrabenazine drug substance.

Aspect 35. A process for producing a deutetrabenazine drug product for commercial sale comprising obtaining a batch of deutetrabenazine drug product that comprises:
i) an amount of Compound 1 in the batch of deutetrabenazine drug product that is not more than 3 area-% Compound 1, relative to the concentration of deutetrabenazine, based on a determination by an HPLC method or
ii) an amount of Compound 2 in the batch of deutetrabenazine drug product that is not more than 0.4 area-% Compound 2, relative to the concentration of deutetrabenazine, based on a determination by an HPLC method and
preparing the batch deutetrabenazine drug product for commercial sale.

Aspect 36. The process of Aspect 35, wherein the process further comprises determining the amount of the at least one of Compound 1 and Compound 2 in the batch of deutetrabenazine drug product.

Aspect 37. A process of distributing a deutetrabenazine drug product comprising a deutetrabenazine drug substance comprising:
a) obtaining the deutetrabenazine drug product wherein deutetrabenazine drug substance comprises:
i) an amount of Compound 1 in the deutetrabenazine drug substance that is not more than 0.5 area-% Compound 1, relative to the concentration of deutetrabenazine, based on a determination by an HPLC method or
ii) an amount of Compound 2 in the deutetrabenazine drug substance that is not more than 0.15 area-% Compound 2, relative to the concentration of deutetrabenazine, based on a determination by an HPLC method; and
b) distributing the deutetrabenazine drug product comprising the deutetrabenazine drug substance.

Aspect 38. A process of distributing a deutetrabenazine drug product comprising,
a) obtaining the deutetrabenazine drug product that comprises:
i) an amount of Compound 1 in the deutetrabenazine drug product that is not more than 3 area-% Compound 1, relative to the concentration of deutetrabenazine, based on a determination by an HPLC method or
ii) an amount of Compound 2 in the deutetrabenazine drug product that is not more than 0.4 area-% Compound 2, relative to the concentration of deutetrabenazine, based on a determination by an HPLC method; and
b) distributing the deutetrabenazine drug product.

Aspect 39. An impurity for use as a reference standard to detect trace amounts of the impurity in a pharmaceutical composition comprising deutetrabenazine, wherein the impurity is

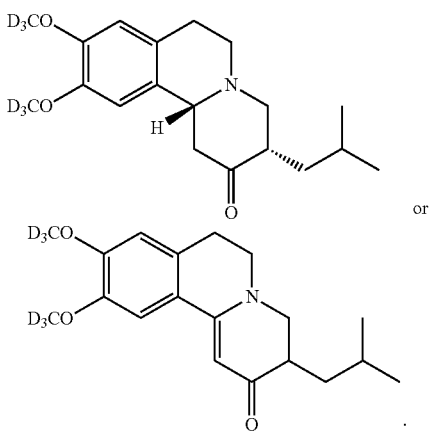

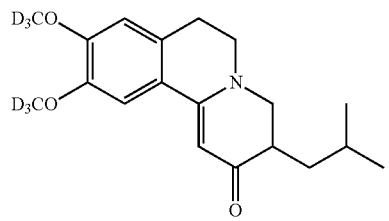

Aspect 40. A method of treating a subject afflicted with a hyperkinetic movement disorder comprising administering to the subject the pharmaceutical composition of any one of Aspects 8-31.

Aspect 41. The method of Aspect 40, wherein the hyperkinetic movement disorder is Huntington's disease.

Aspect 42. The method of Aspect 40 where in the hyperkinetic movement disorder is chorea related to Huntington's disease.

Aspect 43. The method of Aspect 40 where in the hyperkinetic movement disorder is tardive dyskinesia.

Aspect 44. The method of Aspect 40 where in the hyperkinetic movement disorder is a tic associated with Tourette syndrome.

Aspect 45. A process for validating a batch of a pharmaceutical product containing deutetrabenazine and a pharmaceutically acceptable carrier for distribution comprising:
a) determining the amount of at least one of Compound 1 and Compound 2 in the batch; and
b) validating the batch for distribution only if
i) the batch is determined to have not more than 3 area-% Compound 1, relative to the concentration of deutetrabenazine, or
ii) the batch is determined to have not more than 0.4 area-% Compound 2, relative to the concentration of deutetrabenazine.

Aspect 46. A process for preparing a validated pharmaceutical composition comprising deutetrabenazine comprising:
a) obtaining a batch of deutetrabenazine drug substance;
b) determining the amount of at least one of Compound 1and Compound 2 in the batch; and
c) preparing the pharmaceutical composition from the batch only if
i) the batch is determined to have not more than 0.5% Compound 1, relative to the concentration of deutetrabenazine, or
ii) the batch is determined to have not more than 0.15% Compound 2, relative to the concentration of deutetrabenazine

What is claimed is:

1. A process for preparing a deutetrabenazine drug product in the form of a tablet, that has no more than 0.4 area-% of Compound 2 relative to the concentration of deutetrabenazine in the drug product after storage at room temperature for one month, comprising:

obtaining a deutetrabenazine drug substance comprising Compound 2 in an amount that is not more than 0.15 area-%, relative to the concentration of the deutetrabenazine in the deutetrabenazine drug substance;

wherein the amount of Compound 2 is determined by an HPLC method comprising a C18, 150×4.6 mm, 3.5 μm column and a photodiode array/ultraviolet detector at 220 nm; and admixing the deutetrabenazine drug substance with an excipient to produce the deutetrabenazine drug product in the form of a tablet;

wherein the deutetrabenazine drug product has no more than 0.4 area-% of Compound 2, relative to the concentration of deutetrabenazine in the drug product, based on a determination by the HPLC method, after the storage at room temperature for one month.

2. A deutetrabenazine drug product in the form of a tablet produced according to the process of claim 1.

3. The process of claim 1, wherein the amount of Compound 2 in the deutetrabenazine drug substance is about 0.05 area-% to about 0.15 area-%, relative to the concentration of deutetrabenazine in the drug substance, based on a determination by the HPLC method.

4. The process of claim 1, wherein the amount of Compound 2 in the deutetrabenazine drug substance is about 0.05 area-% to about 0.1 area-%, relative to the concentration of deutetrabenazine in the drug substance, based on a determination by the HPLC method.

5. The process of claim 1, wherein the amount of Compound 2 in the deutetrabenazine drug product is 0.007 area-%, to 0.4 area-%, relative to the concentration of deutetrabenazine in the drug product, based on a determination by the HPLC method, after the storage at room temperature for one month.

6. The process of claim 1, wherein the amount of Compound 2 in the deutetrabenazine drug product is 0.03 area-% to 0.4 area-%, relative to the concentration of deutetrabenazine in the drug product, based on a determination by the HPLC method, after the storage at room temperature for one month.

7. The process of claim 1, wherein the amount of Compound 2 in the deutetrabenazine drug product is 0.1 area-% to 0.4 area-%, relative to the concentration of deutetrabenazine in the drug product, based on a determination by the HPLC method, after the storage at room temperature for one month.

* * * * *